United States Patent [19]
Trick et al.

[11] Patent Number: 4,766,889
[45] Date of Patent: Aug. 30, 1988

[54] INFUSION ERECTILE SYSTEM

[75] Inventors: Robert E. Trick; Garry L. Carter, both of Racine, Wis.

[73] Assignee: Medical Engineering Corporation, Racine, Wis.

[21] Appl. No.: 878,554

[22] Filed: Jun. 26, 1986

[51] Int. Cl.$^4$ .............................................. A61F 2/26
[52] U.S. Cl. ........................................................ 128/79
[58] Field of Search ................... 128/79; 604/131, 153

[56] References Cited

U.S. PATENT DOCUMENTS

| | | | |
|---|---|---|---|
| 4,150,669 | 4/1979 | Latorre | 128/79 |
| 4,265,241 | 5/1981 | Portner et al. | 604/131 |
| 4,496,343 | 1/1985 | Prosl et al. | 604/131 |
| 4,548,607 | 10/1985 | Harris | 604/153 |
| 4,604,994 | 8/1986 | Sealfon | 128/79 |

Primary Examiner—John J. Wilson
Assistant Examiner—Cary E. Stone
Attorney, Agent, or Firm—S. E. Krieger

[57] ABSTRACT

The infusion erectile system prosthesis includes a dispensing device implanted in a scrotal sac or subcutaneously in an area adjacent the scrotal sac. The dispensing device includes a reservoir for storing erection stimulating material and a pumping arrangement for actuating movement of the erection stimulating material from the reservoir through a flow tube that joins the penis. The flow tube penetrates a peripheral portion of the penis and communicates with the corpus cavernosum. Infusion of the erection stimulating material into the corpus cavernosum causes an erection to occur. The pump which actuates movement of the erection stimulating material is actuatable manually or electrically.

15 Claims, 1 Drawing Sheet

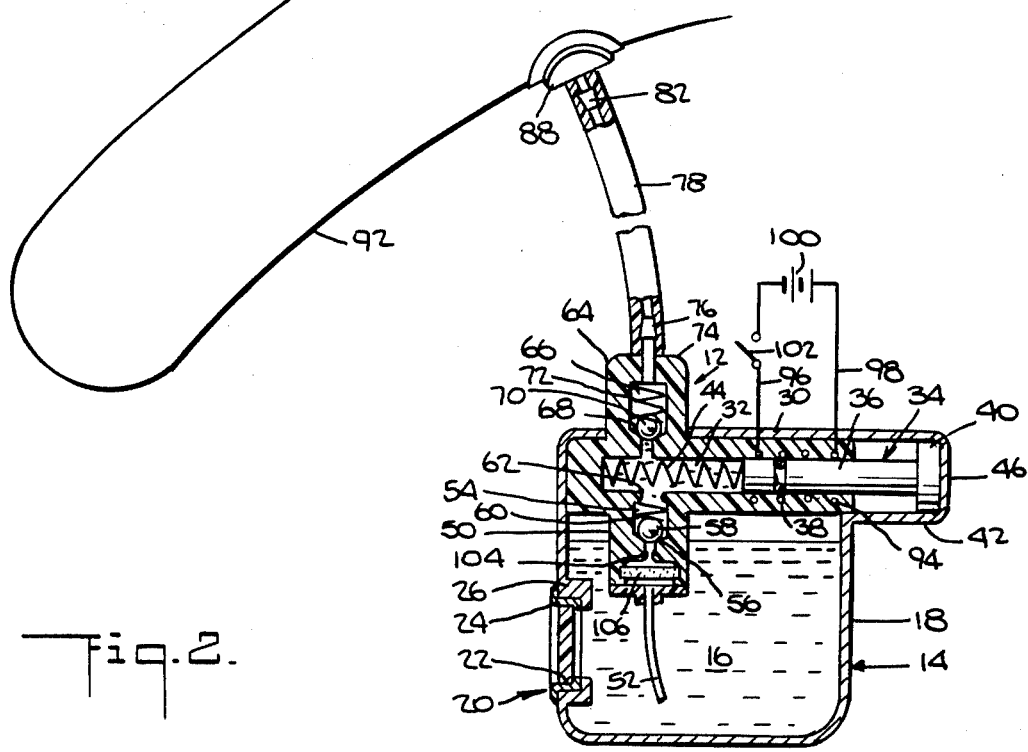
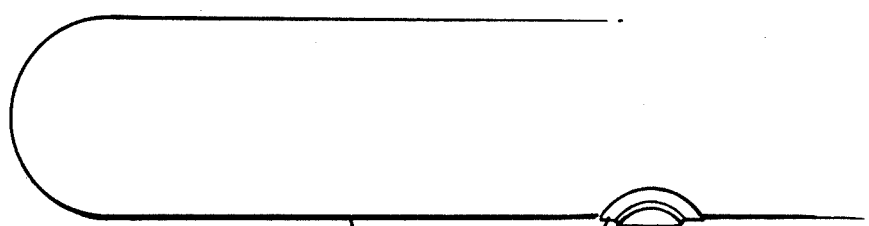
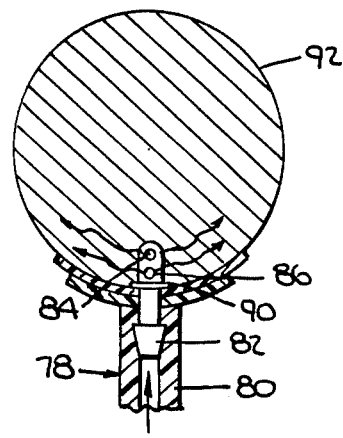
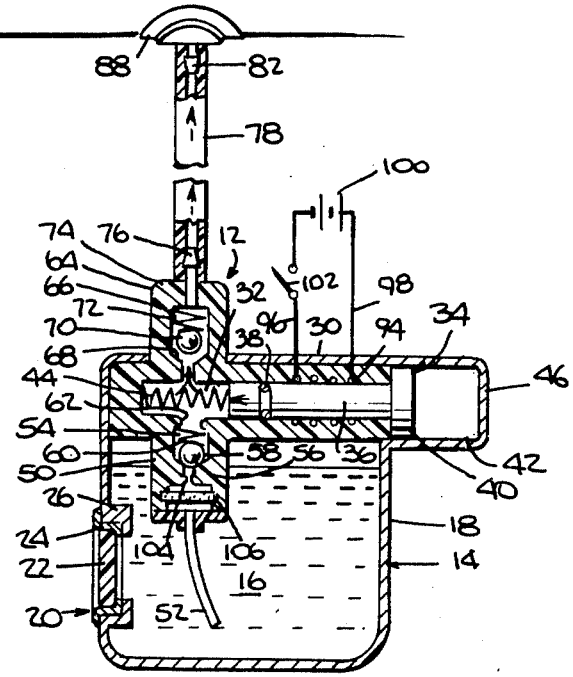

4,766,889

INFUSION ERECTILE SYSTEM

BACKGROUND OF THE INVENTION

This invention relates to penile erection systems for individuals with erectile dysfunction and more particularly to a novel prosthesis and method for stimulating an erection.

Erectile dysfunction is a well known but unfortunately common dilemma often due to organic problems that deleteriously affect the processes which cause an erection.

Attempts to overcome this disability have led to the development of prosthetic devices that are implanted in the penis to mimic an erectile condition. One known prosthetic device such as shown in U.S. Pat. No. 3,832,996, comprises an elongated rigid or semi-rigid plastic material that permanently supports the penis in an erectile condition. This device, because it extends substantially the entire length of the penis can cause discomfort because it does not permit the penis to assume a flaccid condition.

Another known prosthetic device, such as shown in U.S. Pat. No. 4,267,829 includes a segmented prosthesis having generally rigid end sections joined by an intermediate expandable fluid receiving section. The intermediate section, during nonexpansion, is in a normally flaccid condition and thus allows the penis to assume a partially flaccid condition. When a predetermined amount of fluid is received in the intermediate section it expands to form an erectile continuation of the generally rigid end sections thereby establishing an overall erectile condition of the penis. This arrangement, can also be discomforting, since substantially the full extent of the penile body incorporates the implant.

Other known erectile devices such as shown in U.S. Pat. Nos. 4,407,278, 4,224,934, 4,009,711, require implantation in the penis of a prosthetic device that is either inflatable, expandable or includes one or more rigid elements. In accordance with these arrangements an erection is accomplished by expanding the entire prosthetic device or a portion thereof in cooperation with other rigid or semi-rigid inclusions.

The permanent presence of an elongated prosthesis in the penis can be psychologically as well as physically discomforting and the prospect of such discomfort may discourage some individuals with erectile dysfunction from utilizing prosthetic surgery.

It is thus desirable to provide an erectile system and method which stimulates an actual erection of the penis without the need for prosthetic devices which mimic an erection. It is also desirable that such system and method during periods of nonuse permit the entire penis to remain in a normal flaccid condition.

OBJECTS AND SUMMARY OF THE INVENTION

Among the several objects of the invention may be noted the provision of a novel erectile system, a novel erectile system which is based on the infusion of a predetermined amount of an erection stimulating material in the penis, a novel erectile system which permits the subject to store erection stimulating material until needed and to infuse a predetermined amount of such material in the penis when desired, a novel erectile system which can be implanted in the subject to cause an erection by infusion of erection stimulating material into the penis, a novel infusion erectile system which is actuatable by the subject to infuse predetermined amounts of erection stimulating material into the penis, and a novel method for producing an erection in individuals with erectile dysfunction.

Other objects and features of the invention will be in part apparent and in part pointed out hereinafter.

In accordance with the present invention the infusion erectile system includes a device for dispensing erection stimulating material in the penis, which device can be implanted in the scrotal sac or subcutaneously in an adjacent area.

The dispensing device infuses a predetermined amount of the erection stimulating material into the penis through a flow means that is joined to a peripheral portion of the penis. An end portion of the flow means penetrates the penis for communication with the corpus cavernosum.

The erection stimulating material is infused in the penis from a reservoir of the dispenser by means of a pumping arrangement. The dispenser also includes a metering arrangement for metering a predetermined amount of the erection stimulating material that can be pumped into the flow means for infusion into the penis.

The dispenser can be actuated manually or electrically, as by a battery source, and preferably includes a control device that establishes a predetermined minimum time delay before the pump can pump a predetermined required dosage of erection stimulating material.

The erection stimulating material which has been found to provide good results is papaverine, which produces a quality erection in individuals afflicted with various forms of erectile dysfunction. The present invention thus provides a desirable alternative to prosthetic devices which mimic erection.

The invention accordingly comprises the constructions and method hereinafter described, the scope of the invention being indicated in the claims.

DESCRIPTION OF THE DRAWINGS

In the accompanying drawings, in which a preferred embodiment of the invention is illustrated, FIG. 1 is a simplified sectional view of an infusion erectile system prosthesis incorporating one embodiment of the present invention;

FIG. 2 is a view similar to FIG. 1 showing the prosthesis in an actuated position; and, FIG. 3 is a fragmentary sectional view thereof showing distribution of erection stimulating material into the penis.

Corresponding reference characters indicate corresponding parts throughout the several views of the drawings.

DETAILED DESCRIPTION OF THE INVENTION

An infusion erectile system prosthesis incorporating one embodiment of the invention is generally indicated by the reference number 10 in FIG. 1.

The prosthesis 10 includes a generally cylindrical-shaped dispenser 12 with a reservoir section 14 containing an erection stimulating material 16. Preferably the erection stimulating material 16 is a mixture of papaverine and phentolamine in weight ratios of about 30:1 respectively as disclosed in Intracavernous Drug-Induced Erections In The Management of Male Erectile Dysfunction: Experience With 100 Patients by Abraham A. Sidi et al, The Journal of Urology, Vol.

135, April 1986. Accordingly, approximately one bolus of the foregoing papaverine and phentolamine mixture, when infused in the corpus cavernosa of the penis, should stimulate an erectile condition of the penis.

The dispenser 12 has a peripheral shell or housing 18 preferably formed of silicone rubber. A septum 20 is provided at the reservoir section 14 to permit refilling of the reservoir 14 with the erection stimulating material 16.

The septum 20, shown in simplified schematic form, includes a needle penetrable sealing disk 22 joined in leak tight fashion to a cup-shaped support member 24. The support member 24 is likewise held in leak tight fashion by an inwardly-stepped, ring-shaped section 26 formed integrally with the shell 18.

The dispenser 12 further includes a pump section 30, preferably formed of silicone rubber and joined to the interior of the shell 18 over the reservoir section 14. The pump section 30 includes a blind pump channel 32 which slidably accommodates a reciprocable plunger 34 having a stem portion 36 with an O-ring seal 38.

A plunger head 40 is formed at one end of the stem portion 36 and is disposed in a depressible chamber section 42 of the shell 18. A biasing member, such as a spring 44, biases the plunger 34 into a normally retracted position with respect to the pump channel 32, as shown in FIG. 1, wherein the plunger head 40 engages an end wall 46 of the depressible section 42.

The pump section 30 also includes a depending fluid draw section 50 having an extension tube 52 extending into the reservoir 14. The fluid draw section 50 is formed with a draw channel 54 that communicates with the pump channel 32. The draw channel 54 has a valve seat 56 with a ball valve 58. The ball valve 58 closes off the extension tube 52 under the influence of a biasing spring 60 confined in the draw channel by an annular formation 62.

A receiving section 64, formed opposite the fluid draw section 50, includes a receiving channel 66 that communicates with the pump channel 32. The receiving channel 66 includes a valve seat 68 with a ball valve 70. The ball valve 70 closes communication between the receiving channel 66 and the pump channel 32 under the influence of a biasing spring 72. The spring 72 is confined in the receiving channel 66 by a reduced neck portion 74 of the receiving section 64. A tube holder 76 extends from the reduced neck portion 74 for engagement with one end of a flow tube 78.

The flow tube 78, which is preferably formed of silicone rubber is joined at an opposite end 80 to an outlet fitting 82 having dispersion openings such as 84 and 86 (FIG. 3). A suturing disk 88, preferably formed of Dacron or other ingrowth material, is provided between the tube end 80 (FIG. 3) and a flange 90 formed on the outlet fitting 82.

In using the infusion erectile system prosthesis 10, the dispenser 12 is implanted in the scrotal sac (not shown) in any suitable known manner, or in an adjacent area. The implantation is made such that the flow tube 78 is joined to the penis, schematically shown at 92, by suturing the disk 88 to the penis. The suture is accomplished after the outlet fitting 82 has been located in the corpus cavernosa of the penis in any suitable known manner.

When it is desired to stimulate an erection of the penis 92, the user strokes the chamber section 42 of the dispenser 12 to depress the chamber section 42. The chamber 42, since it forms a projection from the generally cylindrical shape of the dispenser 12, is easily detectible by the user. Stroking of the chamber section 42 will move the stem portion 36 of the plunger 34 toward the draw channel 54 and the receiving channel 66, as shown by a comparison of FIGS. 1 and 2.

With the plunger 34 thus protracted in the pump channel 32, any erection stimulating material 16 in the pump channel will be forced into the receiving channel 66 past the ball valve 70. Protracted movement of the plunger 34 will also maintain the ball valve 58 against the valve seat 56 in the draw channel 54 thereby preventing flow of erection stimulating material 16 from the reservoir 18 into the draw channel 54.

The erection stimulating material 16 that has been forced into the receiving channel 66 flows into the flow tube 78 toward the outlet fitting 82 and through the dispersion openings 84 and 86 into the corpus cavernosum of the penis.

The amount of erection stimulating material 16 which flows through the flow tube 78 can be predetermined and is preferably one bolus.

The predetermined amount of erection stimulating fluid is determined by a protraction limit position of the plunger 34 which is defined by engagement of the plunger head 40 with the free end of the pump channel 32 as shown in FIG. 2. After the plunger 34 has reached its protraction limit position, the biasing spring 44 in the pump channel 32 will urge the plunger 34 to a retraction limit position defined by engagement of the plunger 34 with the end wall 46 of the depressible section 42 as shown in FIG. 1. The volume displaced by movement of the plunger stem portion 36 between the protraction limit position and the retraction limit position establishes the predetermined amount of erection stimulating fluid that flows into the draw channel 54 and the flow tube 78.

Retraction of the plunger 34 by the biasing spring 44 causes a suction in the pump channel 32 that unseats the ball valve 58 from the valve seat 56 allowing erection stimulating fluid 16 from the reservoir 18 to flow through the extension tube 52, into the draw channel 54 and the pump channel 32.

The suction attributable to retraction of the plunger 34 also attracts the ball valve 70 against the valve seat 68 in the receiving channel 66, which prevents movement of erection stimulating material into the receiving channel 66 during retraction of the plunger 34.

Thus the arrangement of the ball valves 58 and 70 and the establishment of protraction and retraction limit positions by the free end of the pump channel 32 and the end wall 46 constitute a metering arrangement for metering a predetermined amount of erection stimulating material 16 that can flow through the flow tube 78 during stroking of the plunger 34.

If desired, the stroking of the plunger 34 can be accomplished electrically. Accordingly, a solenoid 94 is provided in the pump section 30 with lead wires 96 and 98 extending out of the shell 18 for connection to a battery 100 and a switch 102. Preferably the battery 100 and the switch 102 are implanted in the scrotal area. The switch 102 can then be actuated through the scrotal skin.

Also, if desired, the plunger 34 can be equipped with a delay means, such as a calibrated orifice 104 which limits the rate of fluid flow from the reservoir 14 into the pump channel 32 to a predetermined amount. Thus a minimum predetermined time must elapse before an effective amount of erection stimulating material 16 flows into the pump channel 32. The purpose of establishing a predetermined minimum time delay before a required predetermined amount of erection stimulating material 16 is transferred to the pump channel 32 is to maintain a recommended time delay period between erection stimulating cycles in accordance with the recommendations of a physician.

A filter 106 can be provided between the orifice 104 and the extension tube 52 to filter out any particulate material that might reside in the reservoir 14.

Since each actuation of the plunger 34 infuses a predetermined amount of erection stimulating material 16 into the penis, it is a relatively simple matter to keep track of the amount of erection stimulating material 16 that has been depleted from the reservoir 14. Consequently, no guesswork is needed to ascertain when the reservoir 14 should be refilled. Refilling is accomplished by penetrating the sealing disk 22 of the septum 20 with a hypodermic needle (not shown) to transfer erection stimulating material into the reservoir 14.

Some advantages of the present invention evident from the foregoing description include a novel infusion erectile system prosthesis which permits the user to synthesize an erection by chemical stimulation. The resulting erection is of substantially the same quality as a normal erection, since it occurs from the same processes that produce a normal erection.

The use of an erection stimulating material thus enables the subject to achieve an erection without the rigid, semi-rigid and expandable prostheses that have long been used to mimic an erection. The omission of expandible devices and rigid implants enable the user to experience a normal flaccid comfortable condition of the penis when there is no need for the erectile condition.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A prosthesis for synthesizing an erection comprising, dispensing means for infusing a first predetermined amount of an erection stimulating material into the penis, said dispensing means including reservoir means for storing a second predetermined amount of said erection stimulating material, flow means communicable with said reservoir means and communicable with said penis for directing flow of said first predetermined amount of erection stimulating material into said penis, and pumping means for actuating movement of said erection stimulating material from said reservoir means through said flow means and into said penis, wherein said pumping means includes control means for enabling said pumping means to pump a predetermined amount of said erection stimulating material only after a predetermined minimum time delay form the last actuation of said pumping means.

2. The prosthesis as claimed in claim 1 wherein said pumping means include a pump chamber and said control means include an orifice for establishing a predetermined rate of flow of said erection stimulating material from said reservoir means to said pump chamber.

3. The prosthesis as claimed in claim 2 wherein said pumping means is manually actuatable.

4. A prosthesis for synthesizing an erection comprising, dispensing means for infusing a first predetermined amount of an erection stimulating material into the penis, said dispensing means including reservoir means for storing a second predetermined amount of said erection stimulating material, flow means communicable with said reservoir means and communicable with said penis for directing flow of said first predetermined amount of erection stimulating material into said penis, and pumping means for actuating movement of said erection stimulating material from said reservoir means through said flow means and into said penis, wherein said flow means include outlet means for outletting the erection material into the penis and attachment means for joining said flow means to said penis to fix the position of said outlet means in said penis.

5. The prosthesis as claimed in claim 4 wherein said erection stimulating material is papaverine.

6. The prosthesis as claimed in claim 4 further including metering means for metering the erection stimulating material moving from said reservoir means to said flow means, to said first predetermined amount.

7. The prosthesis as claimed in claim 6, wherein said metering means meters the first predetermined amount of said erection stimulating material to one bolus.

8. The prothesis as claimed in claim 4, wherein said outlet means includes an outlet member communicable with the corpus cavernosum of the penis.

9. The prosthesis as claimed in claim 8, wherein said flow means include a pair of outlet members communicable with respective corpus cavernosum of said penis.

10. The prosthesis as claimed in claim 4, wherein said reservoir means includes septum means for permitting refill of said reservoir means with said second predetermined amount of said erection stimulating material.

11. The prosthesis as claimed in claim 4, wherein said dispensing means is implanted in a scrotal sac.

12. A method of producing an erection in individuals with erectile dysfunction comprising the steps of:
  (a) implanting a dispensing means for dispensing erection stimulating material, said dispensing means including flow means communicating with the penis for diverting flow of said erection stimulating material into said penis, said flow means including an outlet means for outletting the erection material into the penis;
  (b) securing said flow means to the penis so as to fix the position of the outlet means to the penis; and
  (c) providing means accessible to the individual for controlling the infusion of said erection stimulating material by the dispensing means.

13. The method of claim 12, wherein the erection stimulating material is papaverine.

14. The method of claim 12 wherein the flow means has a member mounted thereon and the step of securing includes suturing the member to the penis.

15. The method of claim 12 wherein the flow means has a disk attached thereto and the step of securing includes suturing the disk to the penis.

* * * * *